US007776332B1

(12) United States Patent
Kuslys et al.

(10) Patent No.: US 7,776,332 B1
(45) Date of Patent: *Aug. 17, 2010

(54) COMPOSITION COMPRISING CASEIN PROTEIN AND WHEY PROTEIN

(75) Inventors: Martinas Kuslys, Grosshoechstetten (CH); Marie-Christine Secretin, Blonay (CH); Rolf Jost, Bolligen (CH); Jean-Claude Maire, S/Lausanne (CH); Olivier Ballevre, Lausanne (CH); Ferdinand Haschke, Lutry (CH); Zdenek Kratky, Maracon (CH); Niklaus Meister, Grosshoechstetten (CH)

(73) Assignee: Nestec S.A., Vevey (CH)

( * ) Notice: Subject to any disclaimer, the term of this patent is extended or adjusted under 35 U.S.C. 154(b) by 1012 days.

This patent is subject to a terminal disclaimer.

(21) Appl. No.: 10/088,766

(22) PCT Filed: Sep. 12, 2000

(86) PCT No.: PCT/EP00/08910

§ 371 (c)(1),
(2), (4) Date: Jun. 20, 2002

(87) PCT Pub. No.: WO01/22837

PCT Pub. Date: Apr. 5, 2001

(30) Foreign Application Priority Data

Sep. 29, 1999 (GB) .................................. 9923048.4

(51) Int. Cl.
*A61K 9/16* (2006.01)
*A61K 39/00* (2006.01)
*A61K 45/00* (2006.01)
*A61K 51/00* (2006.01)

(52) U.S. Cl. ................ 424/157.1; 424/1.11; 424/278.1; 424/418; 424/491; 424/520; 424/535; 426/41; 426/583

(58) Field of Classification Search .................. 530/350; 424/157.1, 278.1, 400, 439; 426/44, 531, 426/569, 583, 648
See application file for complete search history.

(56) References Cited

U.S. PATENT DOCUMENTS

| | | | |
|---|---|---|---|
| 4,485,040 A | | 11/1984 | Roger et al. |
| 5,728,678 A | * | 3/1998 | Trimbo et al. .................. 514/12 |
| 5,916,621 A | * | 6/1999 | Georgi et al. ................. 426/583 |
| 6,777,391 B1 | * | 8/2004 | Kratky et al. .................. 514/23 |
| 6,787,158 B1 | * | 9/2004 | Erdmann et al. ............. 424/535 |

FOREIGN PATENT DOCUMENTS

| | | |
|---|---|---|
| EP | 0418593 | 3/1991 |
| EP | 0 421 309 | 4/1991 |
| EP | 0 880 092 | 12/1998 |
| EP | 0880902 | 12/1998 |
| EP | 0 418 593 | 4/2008 |
| JP | 58-165742 * | 9/1983 |
| WO | WO 93/16595 | 2/1993 |
| WO | 95/17102 | 6/1995 |
| WO | WO 95/17102 * | 6/1995 |
| WO | WO 98/04254 | 5/1998 |

OTHER PUBLICATIONS

XP-002158762.*
Marshall, Casein Macropeptide From Whey—A New Product Opportunity, Food Research Quarterly, vol. 51, Nos. 1 &2, (1991), p. 86-91.
Tanimoto, et al., Large-scale Preparation of k-Casein Glycomacropeptide from Rennet Casein Whey, Biosci, Biotech, Biochem., 56 (1992), p. 140-141.
Heine, et al., The Importance of a-Lactalbumin in Infant Nutrition, American Institute of Nutrition, 121 (1990), p. 277-283.
Heine, et al., a-Lactalbumin-enriched low-protein infant formulas: a comparison to breast milk feeding, Scandinavian University Press, Acta Paediatr. 85 (1996), p. 1024-1028.
Walstra et al., Diary Chemistry and Physics, John Wiley and Sons, 1984, New York, Chapter 1, p. 1-11.
Idem, Appendix, Table A.6, p. 402-403.
Idem, Appendix, Table A.15, p. 416-422.
Alais et al., 1975, Milk proteins: Biochemical and biological aspects, World review of Nutrition and Dietetics, 20: p. 66-167.
Souci Fachman Kraut, Food Composition and Nutrition Tables, Medpharm Scientific Publishers Stuttgart, Boca Raton, 1994, p. 41-46.
USDA Agricultural Research Data. The National Nutrient Database for standard reference. Release 18. Whey, acid, dried. http://www.nal.usda.gov/fnic/foodcomp/egi-bin/list_nut_edit.pl.
International Preliminary Examination Report for PCT/EP00/08910.
Quero, et al., 1997 Reduction of hyperthreonemia in term infants fed a whey predominant formula without glycomacropeptide, Journal of Pediatric Gastroentrology Nutrition, vol. 24, p. 491.
Opposition on behalf of Friesland Brands B.V. to EP 1 220 620 Composition comprising casein protein and whey protein in the name of Societe des Produits Nestle S.A.
Opposition on behalf of Numico Research B.V. to EP 1 220 620 Composition comprising casein protein and whey protein in the name of Societe des Produits Nestle S.A.
Abstract of XP-002158762 Entitled: "Nutrient Composition Baby Infant Contain Casein Whey Isoleucine Leucine Methionine Cystine Phenylalanine Tyrosine Threonine Tryptophan Valine."

* cited by examiner

*Primary Examiner*—Robert B Mondesi
*Assistant Examiner*—J. Hines
(74) *Attorney, Agent, or Firm*—K&L Gates LLP

(57) ABSTRACT

A composition for an infant formula which includes casein protein and whey protein; a method of producing the composition; use of the composition in the manufacture of a medicament or nutritional product for addressing malnutrition; and a method of addressing malnutrition which includes administering an effective amount of the composition are provided. The composition includes protein, free arginine; tryptophan and histidine, a lipid source and a carbohydrate source. In addition, the whey protein is sweet whey protein from which caseino-glyco-macropeptide has been removed.

16 Claims, No Drawings

COMPOSITION COMPRISING CASEIN PROTEIN AND WHEY PROTEIN

CROSS REFERENCE TO RELATED APPLICATIONS

This patent application is a 371 of International Patent Application No. PCT/EP00/08910, filed on Sep. 12, 2000, which claims priority to British Application No. 9923048.4 filed on Sep. 29, 1999.

This invention relates to a composition for an infant formula which comprises casein protein and whey protein; a method of producing the composition; use of the composition in the manufacture of a medicament or nutritional product for addressing malnutrition; and a method of addressing malnutrition which comprises administering an effective amount of the composition.

Within the context of this application the word "comprises" is taken to mean "includes, among other things" and it is not intended to mean "consists of only".

Mother's milk is recommended for all infants. However, in some cases mother's milk is not available and infant formulae must be used. Normal, full-term infants are usually fed cow's-milk-based formulas. These formulas contain a mixture of casein and whey as protein sources and they provide nutrition for infants, however they do not provide a protein concentration and an amino acid profile equivalent to that of mother's milk. In addition these standard formulae are not suitable for pre-term infants and those having adverse reactions to protein in cow's milk formula or to lactose.

An alternatives to cow's milk formula is soy formula; particularly for infants who are lactose intolerant. However, soy is not as good a protein source as cow's milk. Also, infants do not absorb some minerals, such as calcium, as efficiently from soy formulae.

A further alternative formula is based on hydrolysed protein. These formulas are hypoallergenic and have a decreased likelihood of an allergic reaction.

Ideally, to be as close as possible to human milk, the protein in infant formulae may be derived from both whey and casein in an appropriate ratio. However, a problem with conventional formulae having these proteins is that they have a high protein concentration to ensure that the infant gets the necessary amount of all essential amino acids. The protein concentration is higher than the concentration normally found in human milk and it may not be beneficial for an infant because an infant's metabolism is susceptible to overloading with nitrogen from its protein intake.

To address this problem, formulae having improved amino acid profiles have been suggested, for example those having hydrolysed whey proteins. The whey protein may be acid whey protein or sweet whey protein. In general, acid whey protein is preferred from a nutritional point of view since it has a lower threonine content and this is closer to that of human milk. However, until now it has not been possible to provide the advantage of a composition having a protein concentration equivalent to the concentration in human milk and a good amino acid profile in formulae having whey protein and casein. An advantage provided by casein in formulae is that it has the ability to form curd which enhances the feeling of satiety.

The present invention addresses the problems set out above.

SUMMARY OF THE INVENTION

Accordingly, the invention provides a composition for an infant formula which comprises whey protein; casein protein; free arginine; free histidine; and tryptophan rich milk protein, free tryptophan or a mixture thereof.

In a second aspect the invention provides a method of producing the composition which comprises the step of blending whey protein and casein protein together with free arginine; free histidine; and tryptophan rich milk protein, free tryptophan or a mixture thereof and homogenising the blended mixture.

In a third aspect the invention provides use of an embodiment of the composition in the manufacture of a medicament or nutritional product for addressing malnutrition.

In a forth aspect the invention provides a method of addressing malnutrition which comprises administering an effective amount of an embodiment of the composition.

Preferably, tryptophan rich milk protein has a level of about 5% or more of amino acids as tryptophan. More preferably it is about 10% or more.

Preferably, the whey protein is acid whey protein or sweet whey protein from which caseino-glyco-macropeptide has been removed. This provides the advantage of a reduced threonine content and an increased tryptophan content as compared to normal sweet whey and is therefore suitable as a protein source for infants.

Preferably an embodiment of the composition comprises from about 9.0 to about 10.0 w/w % of protein, more preferably about 9.5% w/w %. This corresponds to about 1.8 g protein/100 kcal. An advantage provided by this concentration of protein is that it is equivalent to the amount of protein generally present in human milk and it corresponds to the lower limit tolerated by codex alimentarius.

Preferably an embodiment of the composition comprises about 0.5% to about 3% by weight of arginine; tryptophan and histidine. Surprisingly, it has been found that by supplementing the sweet whey fraction with the free amino acids arginine, tyrosine, and histidine, the protein source has an amino acid profile which is close to that of human milk.

Additional features and advantages of the present invention will be described in and apparent from the detailed description of the presently preferred embodiments and the figures.

DETAILED DESCRIPTION OF THE INVENTION

The present invention provides, in an embodiment, improved infant formula.

Preferably an embodiment of the composition comprises a lipid source, a carbohydrate source, and a protein source. This provides the advantage that the composition is as close as possible in content to mothers milk.

Preferably an embodiment of the composition comprises whey protein which is non-hydrolysed. In alternative embodiments it is hydrolysed.

Preferably, the sweet whey fraction is substantially free of lactose. This has the advantage that the infant formula has reduced levels of lysine blockage.

Preferably an embodiment of the composition comprises about 6% to about 50% by weight of whey protein, more preferably about 20% to 40% whey protein, most preferably 30% whey protein. Preferably it comprises from about 20% to about 40% casein protein, more preferably about 30%. Most preferably, the ratio of whey protein to casein protein is about 60%:about 40% to about 70%:about 30%.

Preferably the free amino acids are in free base form.

In one embodiment the composition is suitable for a pre-term infant formula and comprises about 0% to about 0.1% by weight histidine, about 0.1% to about 0.3% by weight arginine, and about 0.3 to about 0.5% by weight tryptophan.

In an alternative embodiment the composition is suitable for a full-term, hypoallergenic infant formula in which the protein source preferably comprises about 0.2% to about 0.4% by weight histidine, about 1% to about 2% by weight arginine, and about 0.2% to about 0.4% by weight tryptophan.

Preferably the concentration of tryptophan in the composition is at least about 135 mg/g and the concentration of threonine in the composition is less than about 350 mg/g. Preferably the threonine concentration corresponds to about 4.9 g per 100 g protein to about 5.1 g per 100 g protein.

The carbohydrate source may include lactose. The lactose may be the sole source of carbohydrates.

Embodiments of the invention are now described by way of example. As used herein, the abbreviations MPa and SNF represent megapascal and solids-not-fat, respectively.

The invention provides a composition for an infant formula which comprises arginine, tryptophan, histidine and a sweet whey fraction from which caseino-glyco-macropeptide has been removed. The infant formula may be used for pre-term or full-term infants.

The sweet whey used in the protein source may be obtained from cheese making, particularly the sweet whey obtained after the coagulation of casein by rennet. The sweet whey may then be processed as desired. For example, the sweet whey may be treated to remove minerals (cations, anions), lactose, or any of these substances. The sweet whey may be concentrated as desired. Suitable sweet whey sources are commercially available. It is particularly preferred that the sweet whey is substantially lactose-free.

The sweet whey is then treated to remove caseino-glyco-macropeptide. This may be accomplished by any suitable process. One suitable process is described in European patent application 0880902, the disclosure of which is incorporated by reference. In this process, the pH of the sweet whey is adjusted to 1 to 4.3, if necessary. The sweet whey is then contacted with a weakly anionic resin which is predominantly alkaline until the pH of the sweet whey stabilises at about 4.5 to 5.5. The sweet whey fraction from which the caseino-glyco-macropeptide has been removed, is then collected.

In an embodiment of the composition the whey protein is non-hydrolysed. In an alternative embodiment, the sweet whey fraction is hydrolysed to prevent allergic reactions in infants at risk and to make the protein easier to digest. The hydrolysis process may be carried out as desired and is known in the art. In general, the whey protein hydrolysate is prepared by enzymatically hydrolyzing the sweet whey fraction in one or more steps. For example, for an extensively hydrolysed protein, the sweet whey proteins may be subjected to triple hydrolysis using, for example, ALCALASE 2.4 L (EC 940459), then NEUTRASE 0.5 L (obtainable from NOVO NORDISK FERMENT AG) and then pancreatin at 55° C. Alternatively, for a less hydrolysed protein, the sweet whey may be subjected to double hydrolysis using, for example, NOVOZYMES and then pancreatin.

If the sweet whey fraction used is substantially lactose free, it is found that the protein is subjected to much less lysine blockage during the hydrolysis process. This enables the extent of lysine blockage to be reduced from about 15% by weight of total lysine to less than about 10% by weight of lysine; for example about 7% by weight of lysine. This greatly improves the nutritional quality of the protein source.

The free amino acids L-arginine, L-tyrptophan and L-histidine are included in the protein source. Preferably, they are in the form of free amino acids and make up about 1.5% to about 3% by weight of the protein source. For example, the free amino acids may make up about 2% to about 2.6% by weight of the protein source.

In particular, for pre-term formulas, histidine preferably provides about 1% to about 1.5% by weight, arginine preferably provides about 0.6% to about 0.9% by weight, and tyrptophan preferably provides about 0.3% to about 0.5% by weight, of the protein source. For hypoallergenic formulas, histidine preferably provides about 0.2% to about 0.4% by weight, arginine preferably provides about 1% to about 2% by weight, and tyrptophan preferably provides about 0.2% to about 0.4% by weight, of the protein source.

The protein source may include other free amino acids as desired.

The carbohydrate source in the infant formula can be carbohydrate suitable for use in infant formulas. Preferred carbohydrate sources are selected from the group which comprises sucrose, maltodextrin, maltose, lactose, corn syrup, corn syrup solids, rice syrup solids, rice starch, and the like. Preferably, the carbohydrate source includes lactose and maltodextrin. The lactose is preferably free of any allergens. For full term formulas, the carbohydrate source is preferably lactose.

The lipid source may be any lipid or fat which is suitable for use in infant formulas. Preferred lipid sources include milk fat, safflower oil, egg yolk lipid, canola oil, olive oil, coconut oil, palm oil, palm kernel oil, palm olein, soybean oil, sunflower oil, fish oil, and microbial fermentation oil containing long-chain, polyunsaturated fatty acids. These oils may be in the form of high oleic forms such as high oleic sunflower oil and high oleic safflower oil. The lipid source may also be in the form of fractions derived from these oils such as palm olein, medium chain triglycerides (MCT), and esters of fatty acids such as arachidonic acid, linoleic acid, palmitic acid, stearic acid, docosahexaeonic acid, linolenic acid, oleic acid, lauric acid, capric acid, caprylic acid, caproic acid, and the like.

For pre-term formulas, the lipid source preferably contains medium chain triglycerides; for example in an amount of about 15% to about 35% by weight of the lipid source.

The lipid source preferably has a ratio of n-6 to n-3 fatty acids of about 5:1 to about 15:1; for example about 8:1 to about 10:1.

The infant formula may further comprise ingredients which are designed to meet the nutritional needs of a human infant. In particular, it is preferred that the infant formula is "nutritionally complete"; that is it contains adequate nutrients to sustain healthy human life for extended periods.

The amount of protein per 100 kcal of formula is typically about 1.8 g to about 4.5 g; for example about 1.8 g to about 4 g. For full term hypoallergenic formulas, the amount may be about 1.8 g/100 kcal to about 2.5 g/100 kcal. In order to reduce protein loading, the amount may be less than about 2 g/100 kcal. For pre-term formulas, the amount may be about 2.5 g/100 kcal to about 4 g/100 kcal.

The amount of lipid source per 100 kcal of formula may be about 3.3 g to about 6.5 g; for example about 4.4 g to about 6.5 g. The amount of carbohydrate source per 100 kcal of total formula is typically about 7 g to about 14 g.

When in nutritionally complete form, the infant formula contains all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin $B_1$, vitamin $B_2$, vitamin $B_6$, vitamin $B_{12}$, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the infant formula may contain emulsifiers and stabilisers such as soy lecithin, citric acid esters of mono- and di-glycerides, and the like. This is especially the case if the formula is provided in liquid form.

The infant formula may optionally contain other substances which may have a beneficial effect such as fibres, lactoferrin, nucleotides, nucleosides, and the like.

The infant formula may be prepared in any suitable manner. For example, for an infant formula may be prepared by blending together the protein source, the carbohydrate source, and the fat source in appropriate proportions. If used, the emulsifiers may be included in the blend. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

The liquid mixture may then be cooled to about 60° C. to about 85° C.; for example by flash cooling. The liquid mixture may then be homogenised; for example in two stages at about 7 MPa to about 40 MPa in the first stage and about 2 MPa to about 14 MPa in the second stage. The homogenised mixture may then be further cooled to add any heat sensitive components; such as vitamins and minerals. The pH and solids content of the homogenised mixture is conveniently standardised at this point.

If it is desired to produce a powdered infant formula, the homogenised mixture is transferred to a suitable drying apparatus such as a spray drier or freeze drier and converted to powder. The powder should have a moisture content of less than about 5% by weight.

If it is desired to produce a liquid infant formula, the homogenised mixture is filled into suitable containers; preferably aseptically. However, the liquid infant formula may also be retorted in the container. Suitable apparatus for carrying out filling of this nature is commercially available. The liquid infant formula may be in the form of a ready to feed formula having a solids content of about 10 to about 14% by weight or may be in the form of a concentrate; usually of solids content of about 20 to about 26% by weight.

By way of example and not limitation, examples of the present invention will now be given.

Example 1 a) A sweet whey protein concentrate is dissolved in deionised water and the pH is adjusted to 4.25 by contacting the solution with a cation exchange resin (IMAC HP 1100 E, Rohm and Haas). The solution is treated with a weakly anionic resin (IMAC HP 661, Rohm & Haas, which has been regenerated in OH⁻ form) for about 6 hours at 8° C. Once the pH reaches about 5.25 and does not change, the solution is recovered. Over 85% of the caseino-glyco-macropeptide originally present has been removed from the solution.

b) The solution of step a) is standardised in demineralised water at 55° C. The solution is then heated to 75° C. for 20 seconds. The pH of the solution is adjusted to 7.5 by the addition of $Ca(OH)_2$ and a solution of NaOH and KOH.

The reaction mixture is then subjected to microfiltration and ultrafiltration and then dried by lyophilisation and packaged into metal cans. The protein has low levels of lysine blockage with 6.9% blocked lysine and 9% reactive lysine.

c) The protein of step b) is combined with 0.72% by weight L-arginine, 0.44% by weight of L-tyrptophan, and 1.38% by weight of L-histidine. The mixture is formulated into a powdered infant formula. The infant formula has the following composition:

| Component | Amount |
| --- | --- |
| Milk SNF | 8-10% |
| Whey protein | 6-50% |
| Alpha-lactalbumin rich whey protein source | 0-2% |
| Arginine | 0.1-0.3% |
| Histidine | 0-0.1% |
| Fat | 25-30% |
| Lactose | 10-40% |
| Vitamins and minerals | To meet regulations |

The composition has a protein concentration of 9.5 w/w % or 1.8 g protein/100 kcal.

A composition for an infant formula which comprises casein protein and whey protein; a method of producing the composition; use of the composition in the manufacture of a medicament or nutritional product for addressing malnutrition; and a method of addressing malnutrition which comprises administering an effective amount of the composition. A preferred embodiment of the composition comprises non-hydrolysed protein, free arginine; tryptophan and histidine, a lipid source and a carbohydrate source. In addition, the whey protein is acid whey protein or sweet whey protein from which caseino-glyco-macropeptide has been removed.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A composition for an infant formula comprising: whey protein, wherein the whey protein is hydrolysed sweet whey protein from which caseino-glyco-macropeptide has been removed; casein protein; free arginine; free histidine; and a milk protein comprising 5% or more of tryptophan.

2. The composition according to claim 1 which comprises 1.5% to 3% by weight of arginine; tryptophan and histidine.

3. The composition according to claim 1 which comprises a lipid source, a carbohydrate source, and a protein source.

4. The composition according to claim 1 wherein the whey protein is treated to remove lactose.

5. The composition according to claim 1 which comprises 6% to 50% by weight of whey protein and 20% to 40% casein protein.

6. The composition according to claim 1 which comprises 0% to 0.1% by weight histidine, 0.1% to about 0.3% by weight arginine, and 0.3 to 0.5% by weight tryptophan.

7. The composition according to claim 1 which comprises 0.2% to 0.4% by weight histidine, 1% to 2% by weight arginine, and 0.2% to 0.4% by weight tryptophan.

8. A method of producing an infant formula, the method comprising blending whey protein, wherein the whey protein is hydrolysed sweet whey protein from which caseino-glyco-macropeptide has been removed, and casein protein together with free arginine; free histidine; a milk protein comprising 5% or more of tryptophan and homogenising the blended mixture.

9. An infant formula comprising:
hydrolysed sweet whey protein, from which caseino-glyco-macropeptide has been removed;
casein protein;
free arginine;
free histidine; and
a milk protein comprising 5% or more tryptophan.

10. The infant formula of claim 9 comprising from 9.0 to 10.0 w/w % of all protein sources contained in the infant formula.

11. The infant formula of claim 9 comprising 1.5% to 3% by weight of arginine; tryptophan and histidine.

12. The infant formula of claim 9 comprising a lipid source, a carbohydrate source, and a protein source.

13. The infant formula of claim 9 comprising 6% to 50% by weight of whey protein and 20% to 40% casein protein.

14. The infant formula of claim 9 comprising 0.1% to 0.3% by weight arginine, and 0.3 to 0.5% by weight tryptophan.

15. The infant formula of claim 9 comprising 0.2% to 0.4% by weight histidine, 1% to 2% by weight arginine, and 0.2% to 0.4% by weight tryptophan.

16. A method of providing nutrition to an infant, the method comprising administering to the infant a composition comprising whey protein, wherein the whey protein is hydrolysed sweet whey protein from which caseino-glyco-macropeptide has been removed; casein protein; free arginine; free histidine; and a milk protein comprising 5% or more of tryptophan.

* * * * *